United States Patent
Shamblee et al.

(10) Patent No.: US 7,034,177 B2
(45) Date of Patent: Apr. 25, 2006

(54) PROCESS OF MAKING PHOSPHORDIAMIDITE COMPOUNDS

(75) Inventors: Dwight Shamblee, North Charleston, SC (US); Shiming Wo, Summerville, SC (US); Bing Wang, Summerville, SC (US)

(73) Assignee: Rhodia Inc, Cranbury, NJ (US)

( * ) Notice: Subject to any disclaimer, the term of this patent is extended or adjusted under 35 U.S.C. 154(b) by 163 days.

(21) Appl. No.: 10/457,177

(22) Filed: Jun. 9, 2003

(65) Prior Publication Data
US 2003/0236233 A1 Dec. 25, 2003

Related U.S. Application Data

(60) Provisional application No. 60/388,224, filed on Jun. 13, 2002.

(51) Int. Cl.
*C07F 9/22* (2006.01)

(52) U.S. Cl. ........................................ 558/192; 558/167

(58) Field of Classification Search ................ 558/167, 558/192
See application file for complete search history.

(56) References Cited

U.S. PATENT DOCUMENTS

| 2,085,784 A | * | 7/1937 | Bottoms ....................... 562/554 |
| 5,412,088 A | * | 5/1995 | Jones et al. ............... 536/27.81 |
| 5,705,621 A | | 1/1998 | Ravikumar |
| 5,863,905 A | | 1/1999 | Suhadolnik et al. |

FOREIGN PATENT DOCUMENTS

WO　　WO 97/42208　　11/1997

OTHER PUBLICATIONS

Qu-Ming Gu et al., "Synthesis of Phosphotriester Analogues of the Phosphoinositides PtdIns(4,5)$P_2$ and PtdIns(3,4,5)$P_3$", Jul. 1, 1996, pp. 8642-8647.

* cited by examiner

Primary Examiner—Johann Richter
Assistant Examiner—Ebenezer Sackey
(74) Attorney, Agent, or Firm—Watov & Kipnes, P.C.

(57) ABSTRACT

A process of producing cyanoalkyl tetraalkylphosphordiamidites at least substantially free of amine hydrohalide with improved storage stability.

16 Claims, No Drawings

PROCESS OF MAKING PHOSPHORDIAMIDITE COMPOUNDS

RELATED APPLICATION

This application claims priority of U.S. Provisional Patent Application Ser. No. 60/388,224 filed on Jun. 13, 2002.

FIELD OF THE INVENTION

The present invention is generally directed to the production of phosphordiamidite compounds which serve as key reagents for the preparation of, for example, antisense drugs. The present process facilitates the removal of undesirable amine hydrohalide compounds which are typically present in the reaction media and are carried to the final product. The elimination of such amine hydrohalide byproducts can improve the stability of the final product.

BACKGROUND OF THE INVENTION

Phosphordiamidite compounds such as cyanoalkyl tetraalkylphosphordiamidite compounds are key reagents for the preparation of antisense drugs. Typically, such intermediate compounds are prepared by a two-step reaction in which a phosphorus trihalide is reacted with a 2-cyanoalkanol or 2-cyanoalkoxytrialkylsilane to form 2-cyanoalkylphosphordihalidite (NC—$R^1$—O—P—$X_2$ wherein $R^1$ is an alkyl group preferably having from 1 to 6 carbon atoms and X is a halide). The resulting phosphordihalidite compound is reacted with a dialkylamine to give the desired product (cyanoalkyl tetraalkylphosphordiamidite) having the following formula NC—$R^1$—O—P[N($R_2$)]$_2$ wherein each of $R^1$ and R is an alkyl group, preferably having from 1 to 6 carbon atoms. An amine hydrohalide is produced as a byproduct. A major portion of the amine hydrohalide can be removed by filtration but there always remains a small amount of amine hydrohalide dissolved in the reaction media which can adversely affect the storage stability of the cyanoalkyl tetraalkylphosphordiamidite compounds. In particular, the presence of the amine hydrohalide renders the desired product unstable at ambient temperatures over extended periods of time.

It would therefore be a significant advance in the art to provide a method for the production of phosphordiamidites and particularly cyanoalkyl tetraalkylphosphordiamidites in which amine hydrohalide byproducts are removed from the reaction system to the extent that the desired product is stable at ambient temperatures for up to extended periods of time.

SUMMARY OF THE INVENTION

The present invention is generally directed to the production of phosphordiamidites and particularly cyanoalkyl tetraalkylphosphordiamidites in which amine hydrohalides are removed from the reaction media to the extent necessary to achieve a product with desired storage stability.

In accordance with one aspect of the present invention, there is provided a method of producing cyanoalkyl tetraalkylphosphordiamidites comprising:

a) reacting phosphorus trihalide with a cyano-containing reagent to form cyanoalkylphosphordihalidite;

b) reacting the cyanoalkylphosphordihalidite with a dialkylamine to form cyanoalkyl tetraalkylphosphordiamidite and an amine hydrohalide byproduct at least a portion of which is in the form of a precipitate;

c) removing the amine hydrohalide precipitate by filtration to form a filtrate which may contain dissolved amine hydrohalide; and d) treating the filtrate with a substance capable of removing any dissolved amine hydrohalide from said filtrate.

DETAILED DESCRIPTION OF THE INVENTION

The present invention is generally directed to a method of producing cyanoalkyl tetraalkylphosphordiamidites as a reagent for the production of, for example, antisense drugs. The present invention is also directed to the production of a stable form of cyanoalkyl tetraalkylphosphordiamidites which are substantially free of amine hydrohalides.

In the first aspect of the present invention, phosphorus trihalide is reacted with a cyano-containing reagent to form cyanoalkylphosphordihalidite. The cyano-containing reagent is preferably selected from the group consisting of a cyanoalkanol and a cyanoalkoxytrialkylsilane.

The alkanol group of the cyanoalkanol is preferably a $C_1$–$C_6$ alkanol with ethanol being the most preferred alkanol. The alkoxy and alkyl groups of the cyanoalkoxytrialkylsilane preferably have 1–6 carbon atoms with ethoxy and methyl being the preferred alkoxy and alkyl groups, respectively.

With regard to the cyanoalkylphosphordihalidite, the halides can include any halide (e.g. fluorine, chlorine and bromine). Chlorine is the preferred halide. The alkyl groups can be any alkyl group including straight or branch chained alkyl groups, preferably having from 1 to 6 carbon atoms. Ethyl is the preferred alkyl group.

The resulting cyanoalkylphosphordihalidite is reacted with a dialkylamine. The preferred alkyl groups for the dialkylamine have from 1 to 6 carbon atoms. Isopropyl is the preferred alkyl group.

The above-mentioned reaction produces a hydrohalide byproduct which has to be neutralized for the reaction to go to completion. The hydrohalide byproduct can be neutralized by using an excess of a dialkylamine or a tertiary amine (e.g. triethylamine, pyridine and the like). The precipitated portion of the amine hydrohalide can be removed by filtration upon completion of the reaction. In accordance with the present invention, any residual amine hydrohalide may be removed from the product through the use of an adsorbent alone or in the presence of a solvent, or through a reagent which renders the hydrohalide portion of the amine hydrohalide capable of being removed from the reaction system by filtration or the like. An example of such reagents are polymer-supported neutralizing agents such as, for example, triethylammonium methylpolystyrene carbonate and N, N-(diisopropyl) aminomethylpolystyrene. The removal of the amine hydrohalide significantly improves the stability of the product such as, for example, when stored at ambient temperatures over extended periods of time.

The adsorbents which may be used in the present invention are any adsorbents which preferentially absorb the amine hydrohalide from the reaction media. Examples of such adsorbents include, for example, alumina, silica gel, Florisil, Decalite and the like and combinations thereof.

The preferred solvents include tetrahydrofuran, diethyl ether, toluene, hexane and the like and mixtures thereof.

The respective amounts of the adsorbent and solvent is within the routine skill in the art and will be an amount sufficient to adsorb at least substantially all the dissolved residual amine hydrohalide byproduct.

The adsorbed amine hydrohalides may be easily removed together with the adsorbent from the reaction product by filtration to produce a product which is stable at ambient temperatures for extended periods of time including and exceeding 120 days.

EXAMPLES

The following examples are illustrative of embodiments of the invention and are not intended to limit the invention as encompassed by the claims forming part of the application.

Example 1

Preparation and Stabilization of 2-Cyanoethyl-N,N, N',N'-tetraisopropylphosphoro-diamidite (PDA)

2-(cyanoethoxy)dichlororphosphine (CDP) can be easily prepared by various processes described in the prior art. For example, the reaction of phosphorous trichloride ($PCl_3$) with either 2-cyanoethanol or trimethylsilyloxypropionitrile (TMSOP) gives CDP in good yield. If desired, the product can be purified with careful vacuum distillation.

The CDP used in this example, and Example 2 was obtained by reacting $PCl_3$ with TMSOP in a molar ratio of 2:1 in acetonitrile at 5° C. Upon completion of the reaction, the solvent and the excess $PCl_3$ were removed by distillation. The crude product was further purified by vacuum distillation, and gave CDP with greater than 98% purity.

A solution comprising 1.80 moles of freshly distilled 2-(cyanoethoxy) dichlorophosphine (CDP) (310 grams) in 2.9 Kg of tetrahydrofuran (THF) as solvent was stirred and cooled to −12±2° C. under a nitrogen blanket and then treated with 8.12 moles (820 grams) of diisopropylamine over a period of ninety minutes, maintaining a temperature of −10±2° C. Stirring of the slurry was continued at ambient temperature for a period of 72 hours, at which time examination by $^{31}P$ NMR showed no reaction intermediates remaining.

The slurry was filtered through a sintered glass filter to remove diisopropylamine hydrochloride (DIPA.HCl) solids. The clear filtrate was passed through a column of 350 grams of Brockmann activated neutral alumina that had been dried at 165° C. at less than 1 Torr for 16 hours. The filtrate was concentrated on a rotary evaporator at a maximum bath temperature of 45° C. The distilled THF was used to rinse the DIPA.HCl and the alumina to collect additional product, which was combined with the first pass product and then concentrated until the vacuum reached 3 Torr. The yield of the pale yellow syrup was 485 grams (88.5% of theoretical) and the initial assay by $^{31}P$ NMR was 99.7%. Table 1 shows a comparison of the stability of this material (A) vs. a sample prepared in the same manner, but without the alumina treatment (B).

Example 2

Preparation and Stabilization of 2-Cyanoethyl-N,N, N',N'-tetraisopropylphosphoro-diamidite (PDA).

In the same manner as detailed in Example 1, a reaction of 1.44 moles of CDP (248 grams) and 7.21 moles of DIPA (728 grams) in 3.0 Kg of toluene as the solvent showed, after 44 hours at ambient temperature, no evidence by $^{31}P$ NMR that any reaction intermediates remained. The yield of very pale yellow syrup was 458 grams (103% of theoretical) and the initial assay by $^{31}P$ NMR was 97.5%. Table 1 shows a comparison of the stability of this material (C) vs. a sample prepared in the same manner, but without the alumina treatment (D).

TABLE 1

| | PDA Analysis by $^{31}P$ NMR | | | |
|---|---|---|---|---|
| Exp. ID | Alumina Treated? | Reaction Solvent | Initial Assay | 120 days @ 22° C. |
| A | Yes | THE | 99.7 | 98.7 |
| B | No | THF | 98.9 | 94.9 |
| C | Yes | Toluene | 97.5 | 97.6 |
| D | No | Toluene | 98.3 | 93.1 |

What is claimed is:

1. A method of producing cyanoalkyl tetraalkylphosphordiamidite comprising:
    a) reacting phosphorus trihalide with cyano-containing reagent selected from the group consisting of cyanoalkanol and cyanoalkoxytrialkylsilane to form cyanoalkylphosphordihalidite;
    b) reacting the cyanoalkylphosphordihalidite with a dialkylamine to form cyanoalkyl tetraalkylphosphordiamidite and an amine hydrohalide byproduct at least a portion of which is in the form of a precipitate;
    c) removing the amine hydrohalide precipitate by filtration to form a filtrate which may contain dissolved amine hydrohalide; and
    d) treating the filtrate with a substance capable of removing any dissolved amine hydrohalide from the filtrate selected from the group consisting of adsorbents and polymer-supported neutralizing agents.

2. The method of claim 1 wherein the adsorbents are selected from the group consisting of alumina, silica gel, Florisil, Decalite and combinations thereof.

3. The method of claim 1 wherein the polymer-supported neutralizing agents are selected from the group consisting of triethylammonium methylpolystyrene carbonate and N, N-(diisopropyl) aminomethylpolystyrene.

4. The method of claim 1 further comprising removing the adsorbent containing the amine hydrohalide.

5. The method of claim 1 wherein the phosphorus trihalide is phosphorus trichloride.

6. The method of claim 1 wherein the alkanol group of the cyanoalkanol has from 1 to 6 carbon atoms.

7. The method of claim 6 wherein the alkanol group is ethanol.

8. The method of claim 1 wherein the alkoxy and alkyl groups of the cyanoalkoxytrialkylsilane have from 1 to 6 carbon atoms.

9. The method of claim 8 wherein the alkoxy group is ethoxy and the alkyl group is methyl.

10. The method of claim 1 wherein the alkyl group of the dialkylamine has from 1 to 6 carbon atoms.

11. The method of claim 1 further comprising neutralizing the hydrohalide by the addition of an excess of a neutralizing amine to precipitate at least a portion of the amine hydrohalide.

12. The method of claim 11 wherein the neutralizing amine is selected from the group consisting of dialkylamines and tertiary amines.

13. The method of claim 1 wherein the adsorbent is employed in the presence of a solvent.

14. The method of claim 13 wherein the solvent is selected from the group consisting of tetrahydrofuran, diethyl ether, toluene, hexane and mixtures thereof.

15. The method of claim 1 wherein the substance capable of removing dissolved amine hydrohalide is a polymer-supported neutralizing agent.

16. The method of claim 15 wherein the polymer-supported neutralizing agent is selected from the group consisting of triethylammonium methylpolystyrene carbonate and N, N-(diisopropyl)aminomethylpolystyrene.

* * * * *